United States Patent [19]

Fields, Jr. et al.

[11] Patent Number: 4,898,972

[45] Date of Patent: Feb. 6, 1990

[54] PROCESS FOR PRODUCING N-PHOSPHONOMETHYLGLYCINE

[75] Inventors: Donald L. Fields, Jr., Manchester; Raymond C. Grabiak, Maryland Heights; Dennis P. Riley, Chesterfield, all of Mo.

[73] Assignee: Monsanto Company, St. Louis, Mo.

[21] Appl. No.: 248,663

[22] Filed: Sep. 26, 1988

[51] Int. Cl.$^4$ ................................................ C07F 9/38
[52] U.S. Cl. ...................................................... 562/17
[58] Field of Search ......................................... 562/17

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 3,969,398 | 7/1976 | Hershman | 260/502.5 |
| 4,853,159 | 8/1989 | Riley et al. | 562/17 |

FOREIGN PATENT DOCUMENTS 011706 1/1981 Hungary .

OTHER PUBLICATIONS

Metal-Catalyzed Oxidations of Organic Compounds, Roger A. Sheldon, Jay K. Kochi, Academic Press, New York London Toronto Sydney San Francisco 1981 pp. 126–129.

*Primary Examiner*—J. E. Evans
*Attorney, Agent, or Firm*—Frank D. Shearin

[57] ABSTRACT

N-phosphonomethylglycine can be produced by contacting N-phosphonomethyliminodiacetic acid with a molecular oxygen-containing gas in the presence of an effective amount of a catalyst selected from the group consisting of the salts and salt complexes of manganese and cobalt, and an effective amount of bromide ion.

17 Claims, No Drawings

PROCESS FOR PRODUCING N-PHOSPHONOMETHYLGLYCINE

BACKGROUND OF THE INVENTION

This invention relates to a process for preparing N-phosphonomethylglycine by the oxidation of N-phosphonomethyliminodiacetic acid using a homogeneous catalyst system. More particularly, this invention relates to a process for producing N-phosphonomethylglycine by the oxidation of N-phosphonomethyliminodiacetic acid using a salt of cobalt or manganese in the presence of bromide ions.

N-phosphonomethylglycine, known in the agricultural chemical art as glyphosate, is a highly effective and commercially important phytotoxicant useful in controlling the growth of germinating seeds, emerging seedlings, maturing and established woody and herbaceous vegetation and aquatic plants. N-phosphonomethylglycine and its salts are conveniently applied in an aqueous formulation as a post emergent phytotoxicant for the control of numerous plant species. N-phosphonomethylglycine and its salts are characterized by broad spectrum activity, i.e., the controlled growth of a wide variety of plants.

Numerous methods are known in the art for the oxidation of N-phosphonomethyliminodiacetic acid to N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst consisting essentially of activated carbon. U.S. Pat. No. 3,950,402 discloses a method wherein N-phosphonomethyliminodiacetic acid is oxidized to N-phosphonomethylglycine in an aqueous media using a free oxygen-containing gas and a noble metal catalyst, such as palladium, platinum or rhodium on a support. U.S. Pat. No. 3,954,848 discloses the oxidation of N-phosphonomethyliminodiacetic acid with hydrogen peroxide and an acid such as sulfuric or acetic acid. Hungarian Patent Application No. 011706 discloses the oxidation of N-phosphonomethyliminodiacetic acid with peroxide in the presence of metals or metal compounds.

There are many references in the literature on the oxidation of alkylaromatic hydrocarbons to aromatic acids in the presence of various catalyst systems. For example, Sheldon and Kochi, *Metal-Catalyzed Oxidations of Organic Compounds*, Academic Press, New York (1981), pages 126–129, discloses that bromide, as hydrogen bromide, sodium bromide, or organic bromide, has a pronounced synergistic effect on the cobalt- and manganese-catalyzed autoxidations of alkylaromatic hydrocarbons.

Although satisfactory results are achieved by the above prior art processes for oxidizing N-phosphonomethyliminodiacetic acid to N-phosphonomethylglycine using heterogeneous catalysts such as activated carbon or platinum deposited on activated carbon, or the use of an acid catalyzed reaction such as the use of sulfuric acid, there is still a need for improved processes to prepare N-phosphonomethylglycine in high yields, which minimizes the formation of undesirable byproducts, such as phosphate.

SUMMARY OF THE INVENTION

These and other advantages are achieved by a process for the production of N-phosphonomethylglycine which comprises contacting N-phosphonomethyliminodiacetic acid with a molecular oxygen-containing gas in the presence of an effective amount of a catalyst selected from the group consisting of the salts and salt complexes of manganese and cobalt and an effective amount of bromide ion.

DETAILED DESCRIPTION OF THE INVENTION

The process of the present invention involves contacting N-phosphonomethyliminodiacetic acid with a salt or salt complex of cobalt and/or manganese in a mixture or solution in the presence of bromide ion. The mixture or solution is contacted with a molecular oxygen-containing gas while heating the reaction mass to a temperature sufficiently high to initiate and sustain the oxidation reaction of N-phosphonomethyliminodiacetic acid to produce N-phosphonomethylglycine.

The catalyst in the present invention can be any one or more of cobalt and manganese salts known to those skilled in the art, such as manganese acetate, manganese sulfate and complexes such as manganese (II or III) acetylacetonate, or cobalt salts such as cobalt sulfate, cobalt (II or III) acetoacetonate salts, cobalt chloride, cobalt bromide, cobalt nitrate and cobalt acetate.

The catalyst can be added to the N-phosphonomethyliminodiacetic acid in the salt form or the salt may be generated in situ by the addition of a source of a cobalt or manganese metal ion, such as manganese dioxide which dissolves in the reaction mixture. However, it should be noted that the manganese chloro(phthalocyaninato) ion is not catalytic under conditions set forth in the examples.

The concentration of the cobalt or manganese catalyst in the process of the present invention can vary within wide limits. The concentration of the catalyst can vary between 1 molar to 0.0001 molar total metal ion concentration. For both cobalt and manganese, the reaction appears to have a first order dependency on the catalyst concentration, i.e., the reaction rate increases linearly as the catalyst concentration increases. The preferred concentration for the catalyst metal ion is in the range of about 0.1 molar to about 0.001 molar, which gives a suitably fast rate of reaction that can be easily controlled and favors selectivity to N-phosphonomethylglycine.

Any number of sources of bromide ion can be used in the process of the present invention such as elemental bromine, or a bromine salt such as ammonium bromide, the alkaline earth bromides, or the alkali metal bromides, which include sodium bromide, potassium bromide and the like.

The concentration of bromide ion in the process of the present invention can vary within wide limits. It is convenient to relate the bromide ion concentration to the concentration of N-phosphonomethyliminodiacetic acid. At a mole ratio of bromide ion to N-phosphonomethyliminodiacetic acid of 0.05 to one or less, only small benefits are seen. It is preferred to use a mole ratio of bromide ion to N-phosphonomethyliminodiacetic acid between about 0.05 to one and 0.4 to one, and even more preferred to use a mole ratio between about 0.25 to about 0.35 to one. At a mole ratio of bromide ion to N-phosphonomethyliminodiacetic acid greater than about 0.4 to one, the reaction rate is reduced. A particularly convenient mole ratio of bromide ion to N-phosphonomethyliminodiacetic acid is between about 0.25 and 0.35 to one.

The reaction temperature is sufficient to initiate and sustain the oxidation reaction, in the range of about 50° C. to 150° C. In general, as the reaction temperature increases, the reaction rate increases. To achieve an easily controlled reaction rate and favor selectivity of the reaction to the formation of N-phosphonomethylglycine, a preferred temperature range is from about 70° C. to about 120° C. If high temperatures are used, pressure must be maintained on the reaction system to maintain a liquid phase and prevent boiling for convenience.

To carry out the process of the present invention, it is only necessary to bring N-phosphonomethyliminodiacetic acid together with an effective amount of the manganese or cobalt catalyst salt and an effective amount of bromide ion in the presence of a molecular oxygen-containing gas. The term "molecular oxygen-containing gas" means molecular oxygen gas or any gaseous mixture containing molecular oxygen with one or more diluents which are nonreactive with the oxygen or with the reactant or the products under the conditions of the reaction. Examples of such diluent gases are air, helium, argon, nitrogen or other inert gas or oxygen hydrocarbon mixtures. A preferred source of molecular oxygen is undiluted oxygen gas.

The oxygen concentration, i.e., the partial pressure of oxygen affects the reaction rate and selectivity to the desired N-phosphonomethylglycine. As the partial pressure of oxygen increases, the reaction rate generally increases and the selectivity to N-phosphonomethylglycine increases. The partial pressure of oxygen can be increased by increasing the overall reaction pressure or by increasing the molecular oxygen concentration in the oxygen-containing gas. The partial pressure of oxygen can vary, preferably from about $2.06 \times 10^5 N/m^2$ (30 psig) to $2.06 \times 10^7 N/m^2$ (3000 psig). A more preferred range is from about $3.1 \times 10^6 N/m^2$ (450 psig) to $1.38 \times 10^7 N/m^2$ (2000 psig).

As will occur to those skilled in the art in view of the present disclosure, the manner in which the solution or mixture of N-phosphonomethyliminodiacetic acid is contacted with a molecular oxygen-containing gas in the presence of the cobalt or manganese salt and the bromide ions can vary greatly. For example, the N-phosphonomethyliminodiacetic acid solution can be contacted with the oxygen-containing gas by agitation, such as bubbling, stirring, shaking and the like. The process of the present invention only requires actively contacting the molecular oxygen-containing gas with the aqueous solution or mixture of N-phosphonomethyliminodiacetic acid containing the cobalt or manganese salt catalyst and the bromide ions.

The initial pH of the reaction affects the reaction rate and the selectivity to N-phosphonomethylglycine. For example, with manganese, as the initial pH increases, the reaction rate increases, but the selectivity to N-phosphonomethylglycine decreases. The initial pH of the reaction can vary between about pH 0.1 to about pH 7. A preferred pH range is from about pH 0.1 to about pH 3. The most preferred pH range is the unadjusted pH of the N-phosphonomethyliminodiacetic acid in a water solution which varies with the N-phosphonomethyliminodiacetic acid concentration and the reaction temperature.

The oxidation reaction can take place in a solution or a slurry. For a solution, the initial concentration of the N-phosphonomethyliminodiacetic acid in the reaction mass is a function of the solubility of the N-phosphonomethyliminodiacetic acid in the solvent (i.e. water) at both the desired reaction temperature and the initial pH of the solution. As the solvent temperature and the initial pH changes, the solubility of the N-phosphonomethyliminodiacetic acid changes. When a cobalt salt is used as the catalyst, the preferred initial concentration of the N-phosphonomethyliminodiacetic acid is a saturated slurry containing a solvent system at reaction conditions, which maximizes the yield of N-phosphonomethylglycine in the reaction mass. However, when a manganese salt is used as the catalyst, the initial concentration of the N-phosphonomethyliminodiacetic acid should be less than about 6 wt. % to prevent the manganese from precipitating out of solution and stopping the reaction.

The reaction is typically carried out in an aqueous solvent, i.e. containing at least about 50 wt. % water. A preferred aqueous solvent is distilled, deionized water.

The invention is further illustrated by, but not limited to, the following examples. In all cases the reactions were conducted in an Engineer Autoclave 300 ml pressure reactor in which a stirrer was installed in the head as were 3 additional valved ports that were used as a sample port, a gas inlet and a purged gas outlet. The stirrer maintains sufficient agitation to afford thorough gas-liquid mixing. The indicated amount of catalyst salt and bromide was dissolved or suspended in a distilled deionized water solution containing the indicated amounts of N-phosphonomethyliminodiacetic acid. The reactor was sealed and heated to the indicated reaction temperatures, then pressurized to the indicated pressures with an oxygen gas sweep. Agitation was initiated prior to heating.

The % selectivity to N-phosphonomethylglycine was determined by dividing the moles of N-phosphonomethylglycine and N-formyl-N-phosphonomethylglycine produced by the total moles of N-phosphonomethyliminiodiacetic acid consumed and multiplying by 100. The % conversion was determined by dividing the moles of N-phosphonomethyliminodiacetic acid consumed by the total moles of starting N-phosphonomethyliminodiacetic acid and multiplying by 100.

EXAMPLE 1

This example illustrates the formation of N-phosphonomethylglycine using a manganese acetate catalyst without bromide ion.

Into a titanium autoclave, manufactured by Autoclave Engineers was added N-phosphonomethyliminodiacetic acid (9.08 g, 0.04 mole) and water (100 ml). Thereafter, manganese acetate (1.088 g, 0.006 mol) was added, and the contents were heated to 80° C. under nitrogen, and then for 2 hours at $3.1 \times 10^6 N/m^2$ (450 psig) pressure using an oxygen gas sweep at a flow rate of about 300 cc/minute. Aliquots were taken at 15, 30, 60, 90, 120 and 150 minutes. After 2.5 hours, conversion was greater than 95% but selectivity was less than 10% as determined by HPLC analysis.

EXAMPLE 2

This example illustrates the results that were obtained using a manganese bromide catalyst, but without additional bromide ion.

To the same autoclave as in Example 1 N-phosphonomethyliminodiacetic acid (13.62 g, 0.6 mol) and manganese dibromide tetrahydrate (1.29 g, 0.0045 mol) were added with water (120 ml) and heated to 80° C. under pressure as in Example 1. After about 90 minutes, the reaction mixture was analyzed by HPLC and the analysis indicated that conversion was 67.18% and selectivity was 10.24%.

EXAMPLE 3

This example illustrates the effects of adding elemental bromine along with the manganese bromide catalyst in the process of the present invention.

To the titanium autoclave of Example 1 was added N-phosphonomethyliminodiacetic acid (27.24 g, 0.12 mol), water (120 ml) and manganese dibromide tetrahydrate (2.577 g, 0.0089 mol) and elemental bromine (0.48 g, 0.03 mol). The reaction mixture was heated and pressurized as in Example 1 for 4 hours and 15 minutes. The reaction media was analyzed by HPLC, and it was found that conversion was 99.85%, and the selectivity was 35.07%.

EXAMPLE 4

Using the same autoclave and temperatures and pressures as in Example 3, the autoclave was loaded with N-phosphonomethyliminodiacetic acid (13.62 g, 0.06 mol) water (120 ml) and manganese dibromide tetrahydrate (1.29 g, 0.0045 mol) and sodium bromide (2.4 g, 0.023 mol). After one hour, the reaction mixture was analyzed by HPLC, and it was found that 99.46% of the N-phosphonomethyliminodiacetic acid was converted at a selectivity of 50.45% to N-phosphonomethylglycine.

These Examples 1–4 clearly show that bromide ions have a positive effect on the conversion of N-phosphonomethyliminodiacetic acid to N-phosphonomethylglycine under these reaction conditions.

EXAMPLE 5–18

A series of runs was made using cobalt sulfate heptahydrate catalyst (1.34 g, 0.005 mol) with an oxygen sweep of 300 cc/minute at 1800 psig ($1.24 \times 10^7 N/m^2$) in 100 grams of water. The variables were the bromide concentration, the concentration of N-phosphonomethyliminodiacetic acid (NPID), and temperature. The results after 95% conversion or better are shown in Table I.

TABLE I

| Example | NaBr Grams | NPID In Grams | Temp. (°C.) | Run Time (Hrs.) | Selectivity | PO4 % |
|---|---|---|---|---|---|---|
| 5 | 1.23 | 20.44 | 90 | 3½ | 86.11 | 5.65 |
| 6 | 1.23 | 30.00 | 85 | 6 | 85.60 | 5.30 |
| 7 | 2.46 | 20.44 | 95 | 2½ | 85.20 | 5.99 |
| 8 | 1.23 | 20.44 | 90 | 3½ | 86.70 | 5.79 |
| 9 | 1.23 | 10.87 | 95 | 2 | 84.79 | 4.91 |
| 10 | 2.46 | 10.87 | 90 | 3½ | 87.53 | 5.00 |
| 11 | 1.23 | 30.00 | 95 | 2½ | 82.87 | 7.46 |
| 12 | 2.46 | 20.44 | 85 | 6 | 87.13 | 5.06 |
| 13 | 2.46 | 30.00 | 90 | 4½ | 85.11 | 5.96 |
| 14 | 0 | 30.00 | 90 | 2¾ | 73.36 | 14.45 |
| 15 | 0 | 20.44 | 95 | 1¾ | 78.46 | 10.41 |
| 16 | 0 | 10.87 | 90 | 2½ | 84.85 | 6.52 |
| 17 | 0 | 20.44 | 85 | 4¼ | 84.01 | 7.80 |
| 18 | 1.23 | 10.87 | 85 | 4¼ | 89.33 | 3.72 |

The above results show that the presence of bromide ions increased the selectivity to N-phosphonomethylglycine and reduced the phosphate by-product in the reaction.

EXAMPLE 19

This example illustrates the process of the present invention using different reaction conditions.

To the autoclave of Example 1 was charged N-phosphonomethyliminodiacetic acid (10.87 g, 0.048 mol), water (125 ml), cobalt dibromide hexahydrate (1.6 g, 0.005 mol) and sodium bromide (0.5 g, 0.005 mol). The mixture was heated to 87.5° C. and pressurized to $12.4 \times 10^6 N/m^2$ (1800 psi) with an oxygen sweep for 3.5 hours. After cooling to room temperature, the mixture was analyzed by HPLC. Results showed that 96% of the N-phosphonomethyliminodiacetic acid was converted with a selectivity to N-phosphonomethylglycine of 90.8%

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

What is claimed is:

1. A process for the production of N-phosphonomethylglycine which comprises contacting N-phosphonomethyliminodiacetic acid with a molecular oxygen-containing gas in the presence of an effective amount of a catalyst selected from the group consisting of the salts and salt complexes of manganese and cobalt, and an effective amount of bromide ion.

2. A process of claim 1 wherein the catalyst concentration is between about 1 molar and 0.0001 molar total metal ion concentration.

3. A process of claim 2 wherein the catalyst concentration is between about 0.1 molar and about 0.001 molar.

4. A process of claim 1 wherein the mole ratio of bromide ion to N-phosphonomethyliminodiacetic acid is at least 0.05.

5. A process of claim 4 wherein the mole ratio is between about 0.05 and 0.4.

6. A process of claim 4 wherein the mole ratio is between about 0.25 and 0.35.

7. A process of claim 1 wherein the catalyst is a manganese salt.

8. A process of claim 7 wherein the catalyst concentration is between about 0.1 molar and about 0.001 molar and the mole ratio of bromide ion to N-phosphonomethyliminodiacetic acid is between 0.05 and 0.4.

9. A process of claim 8 wherein the oxygen-containing gas is at a partial pressure of oxygen between about $2.06 \times 10^5 N/m^2$ and $2.06 \times 10^7 N/m^2$.

10. A process of claim 9 wherein the partial pressure of oxygen is between about $3.1 \times 10^6 N/m^2$ and $1.38 \times 10^7 N/m^2$.

11. A process of claim 8 wherein the N-phosphonomethyliminodiacetic acid is in an aqueous media at an initial pH between about pH 0.1 to about pH 3.

12. A process of claim 1 wherein the catalyst is a cobalt salt.

13. A process of claim 12 wherein the catalyst concentration is between about 0.1 molar and about 0.001 molar and the mole ratio of bromide ion to N-phosphonomethyliminodiacetic acid is between about 0.05 and 0.4.

14. A process of claim 13 wherein the oxygen-containing gas is at a partial pressure of oxygen between about $2.06\times10^5 N/m^2$ and $2.06\times10^7 N/m^2$.

15. A process of claim 14 wherein the partial pressure of oxygen is between about $3.1\times10^6 N/m^2$ and $1.38\times10^7 N/m^2$.

16. A process of claim 13 wherein the N-phosphonomethyliminodiacetic acid is in an aqueous media at an initial pH between about pH 0.1 to about pH 3.

17. A process of claim 1 wherein the N-phosphonomethyliminodiacetic acid is in a slurry.

* * * * *